(12) United States Patent
Yin et al.

(10) Patent No.: US 10,053,483 B2
(45) Date of Patent: Aug. 21, 2018

(54) SYNTHESIS PROCESS OF ANTIPARASITIC DRUG SELAMECTIN

(71) Applicant: Zhejiang Hisun Pharmaceutical Co., Ltd., Taizhou (CN)

(72) Inventors: Mingxing Yin, Taizhou (CN); Jianchao Wu, Taizhou (CN); Jian Chai, Taizhou (CN)

(73) Assignee: Zhejiang Hisun Pharmaceutical Co., Ltd. (CN)

( * ) Notice: Subject to any disclaimer, the term of this patent is extended or adjusted under 35 U.S.C. 154(b) by 249 days.

(21) Appl. No.: 14/389,802

(22) PCT Filed: Apr. 2, 2013

(86) PCT No.: PCT/CN2013/073604
§ 371 (c)(1),
(2) Date: Oct. 1, 2014

(87) PCT Pub. No.: WO2013/149577
PCT Pub. Date: Oct. 10, 2013

(65) Prior Publication Data
US 2015/0329581 A1    Nov. 19, 2015

(30) Foreign Application Priority Data

Apr. 3, 2012    (CN) .......................... 2012 1 0102405

(51) Int. Cl.
*C07H 17/08*    (2006.01)
*C07H 1/00*    (2006.01)

(52) U.S. Cl.
CPC .............. *C07H 1/00* (2013.01); *C07H 17/08* (2013.01)

(58) Field of Classification Search
CPC ................................. C07H 1/00; C07H 17/08
USPC ........................................................ 536/7.1
See application file for complete search history.

(56) References Cited

U.S. PATENT DOCUMENTS

| | | | |
|---|---|---|---|
| 4,427,663 A | 1/1984 | Mrozik | |
| 5,229,416 A | 7/1993 | Meinke et al. | |
| 5,981,500 A | 11/1999 | Bishop et al. | |
| 6,605,595 B1 | 8/2003 | Omura et al. | |
| 6,906,184 B1 | 6/2005 | Walshe et al. | |
| 2006/0003963 A1* | 1/2006 | Gong | C07H 19/12 514/49 |

FOREIGN PATENT DOCUMENTS

| | | |
|---|---|---|
| CN | 1099394 A | 3/1995 |
| CN | 1266437 A | 9/2000 |
| CN | 1724553 A | 1/2006 |
| EP | 677054 A1 | 10/1995 |
| EP | 1003764 A1 | 5/2000 |
| JP | 58167591 | 10/1983 |
| JP | 07503020 | 3/1995 |
| JP | 7506361 | 7/1995 |
| JP | 08508043 A | 8/1996 |
| JP | 2000511943 A | 9/2000 |
| JP | 2006517554 A | 7/2006 |
| WO | 9322307 A1 | 11/1993 |
| WO | 94015944 A1 | 7/1994 |
| WO | 9504746 A1 | 2/1995 |
| WO | 99007721 A1 | 2/1999 |
| WO | 0047597 A1 | 8/2000 |
| WO | 2004069853 A1 | 8/2004 |
| WO | 2010065852 A1 | 6/2010 |

OTHER PUBLICATIONS

International Search Report for Application No. PCT/CN2013/073604 dated Jul. 18, 2013.
Shixiang Lv, "The Synthesis of Selamectin and (R)-4-cyano-3-hydroxybutyric acid ethyl ester", Master's Thesis of Northeast Agricultural University, 2009.
Extended European Search Report for Application No. EP13773160 dated Oct. 22, 2015.

* cited by examiner

*Primary Examiner* — Shaojia Anna Jiang
*Assistant Examiner* — Michael C Henry
(74) *Attorney, Agent, or Firm* — Lerner, David, Littenberg, Krumholz & Mentlik, LLP

(57) ABSTRACT

Provided in the present invention are novel key intermediates of selamectin and the preparation method thereof. Also provided is a new synthesis process, using doramectin as a starting material, and obtaining selamectin via hydrogenation, oxidation, oximation and desugaring. The new process of the present invention has few steps, and is simple to operate, high in yield, low in cost and causes little pollution, and is more suitable for large scale industrial production.

9 Claims, No Drawings

SYNTHESIS PROCESS OF ANTIPARASITIC DRUG SELAMECTIN

CROSS-REFERENCE TO RELATED APPLICATIONS

The present application is a national phase entry under 35 U.S.C. § 371 of International Application No. PCT/CN2013/073604, filed on Apr. 2, 2013, published in Chinese, which claims priority from Chinese Patent Application No. 201210102405.7, filed Apr. 3, 2012, the disclosures which are hereby incorporated herein by reference.

FIELD OF THE INVENTION

The present invention relates to synthesis process of antiparasitic drug, in particular, to new synthesis process of selamectin.

BACKGROUND OF THE INVENTION

Selamectin, has a chemical name of (5Z,25S)-25-cyclohexyl-4'-O-de(2,6-dideoxy-3-O-methyl-α-L-arabino-hexopyranosyl)-5-demethoxy-25-de(1-methylpropyl)-22,23-dihydro-5-(hydroxyimino)avermectin A1a (herein "a" indicates natural avermectin, in which the 25-substituent is (s)-sec-butyl, "A" indicates avermectin wherein the 5-substituent is methoxy, number "1" indicates avermectin wherein the double bond is at 22-23 position), and has a chemical formula of

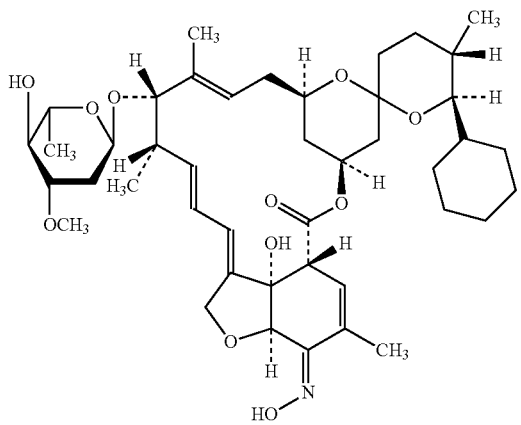

Selamectin is produced by fermentation of new gene-recombined strain of Streptomyces avermitilis, and is a new compound belonging to avermectins. Such new generation antiparasitic drug is developed by Pfizer Inc., America, and is produced by structural modification of doramectin via chemical synthesis.

Selamectin has antiparasitic activity on both endoparasite (threadworm) and ectoparasite (arthropod insects). Having the same effect as other avermectins, selamectin causes rapid, lethal, and non-paralytic neuromuscular paralysis of insects by interfering the glutamic acid-controlling chloride ion channel of the insect. After being applied onto the skin of a cat or a dog, the drug is absorbed into blood, and a part of the drug enters into digestive tract and blood by oral when the animal grooms its hair. The pharmacokinetics results show that selamectin exhibits permanent absorption in blood plasma after topical external application. The experimental data show that selamectin accumulates on skin (in particular sebaceous gland), ensuring a permanent concentration of drug that is sufficient to kill parasitic on the hair. The skin scrapings collected 30 days after the application of the drug can still kill eggs and larva of flea. Therefore, in comparison to conventional similar drugs, selamectin can overcome the disadvantages of poor efficiency, easy recurrence, inconvenient, and poor resistance of pets, and can kill endoparasite and ectoparasite such as flea, heartworm, tick, Itch mite, and ear mite that afflict pet and their owners rapidly, efficiently, conveniently, and completely, and has high safety. Good effect can be obtained by either oral administration or injection.

The synthesis processes of selamectin are reported in the following references: U.S. Pat. No. 5,981,500, EP677054, WO94015944, and CN94101917, wherein selamectin is prepared from doramectin by hydrogenation, desugaring, oxidation and oximation. In the first step of hydrogenation, the compound of formula (II) is prepared by using Wilkinson's catalyst, and toluene as the solvent. The second step, desugaring, is carried out in isopropanol, using sulfuric acid. The third step, oxidation, is carried out in anhydrous ethyl ether, in the presence of active manganese dioxide. The fourth step, oximation, is carried out in anhydrous pyridine, using hydroxylamine hydrochloride. Finally, selamectin is obtained via purification by using silica gel column chromatography. Such process is the basic patented process for the preparation of selamectin, which has the disadvantages of long reaction route, low overall yield, and inconvenient industrial operation.

U.S. Pat. No. 6,906,184, EP1003764, WO99007721, CN98808106, etc. prepare selamectin via three-step chemical synthesis, using doramectin as the starting material. Firstly, the double bond at the C-22, 23 position is converted into single bond by addition reaction, via hydrogenation. The second step is oxidation, only the hydroxyl group at C-5 position is oxidized to ketone. The third step is oximation and desugaring, i.e. the ketone at C-5 position is oximated, while a sugar molecule is desugared, to obtain selamectin. Such process is the improved process of the basic patented process, developed by Pfizer Inc., wherein the reaction that obtains 5-oxime from the intermediate of oxidation product and hydroxylamine hydrochloride, and the hydrolysis step generating monosaccharide derivatives are carried out simultaneously, as a single concurrent reaction, which simplify the operation process significantly, and can reduce the processing and separation process, and thus improve the overall yield and quality of selamectin. However, active manganese dioxide is employed as the oxidant in the second step, with significant amount, which is difficult for after-treatment, and thus the industrial production will bring significant environmental problems. Isopropanol/water system is employed in the third step, i.e. oximation and desugaring, it has long reaction time and is unsuitable for improving the efficiency of industrial production.

Research On the Synthesis Process of Selamectin and Ethyl (R)-4-cyano-3-hydroxybutyrate (Shixiang Lv, Master's Thesis of Northeast Agricultural University, 2009) also uses doramectin as the starting material, wherein selamectin is synthesized via a three-step synthesis. The first step involves the preparation of the compound of formula (II) via catalytic hydrogenation, wherein the reaction condition is optimized, to obtain a yield of 95.8%. In the second step, i.e. oxidation, the intermediate II is prepared by oxidant A addition and oxidant A priming, respectively, and the yield is 93.4%. In the third step, i.e. oximation and desugaring, crude selamectin is obtained, and the optimized reaction conditions, i.e. triethylamine and 45° C., are determined by using triethylamine method and disodium hydrogen phosphate method, changing the reaction concentration, and carrying out reaction at room temperature, and then a yield of 75.5% is obtained. Finally, it is crystallized twice with solvent A, to obtain selamectin (purity >98.5%), and the overall yield is 55%. Such process is a successful improvement developed on the basis of the above mentioned two processes, and has the advantages of short reaction route and mild reaction conditions, and the overall yield is 55%. However, in the second step, i.e. oxidation, the oxidant after-treatment may generate a large amount of heavy metal wastewater, which may restrict the industrial production.

The present invention makes inventive development on the basis of the prior arts, overcomes the disadvantages of the above mentioned processes, and provides a novel synthesis scheme for selamectin, with easy-handled oxidant, short process period, high efficiency, and reduced pollution.

DESCRIPTION OF THE INVENTION

One object of the present invention is to provide novel key intermediates of selamectin (the compound of formula (III) and the compound of formula (IV)) and the preparation method thereof; another object of the present invention is to provide a novel process for the preparation of selamectin according to the above mentioned intermediates.

In one aspect of the present invention, there provides novel intermediates that can be used in the synthesis of selamectin:

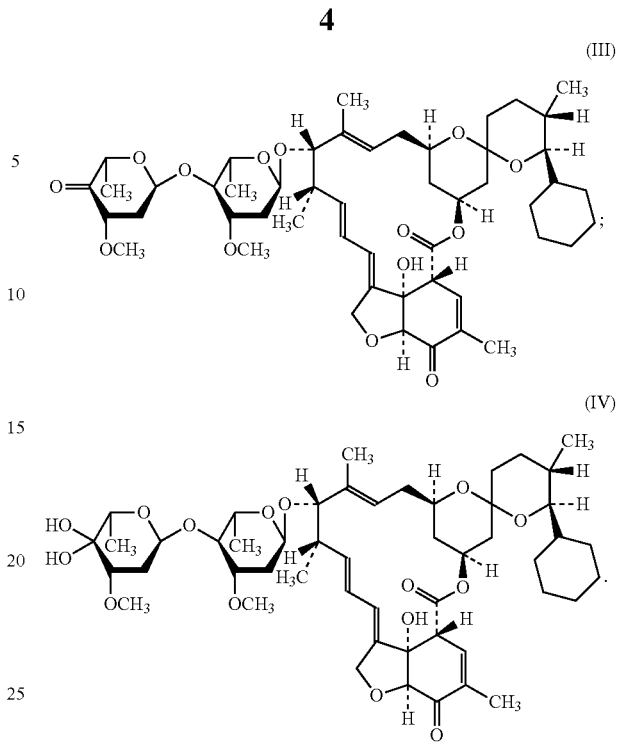

In another aspect of the present invention, there provides a method for the preparation of the compound of formula (III). The method includes the preparation of the compound of formula (III) from the compound of formula (II) via oxidation:

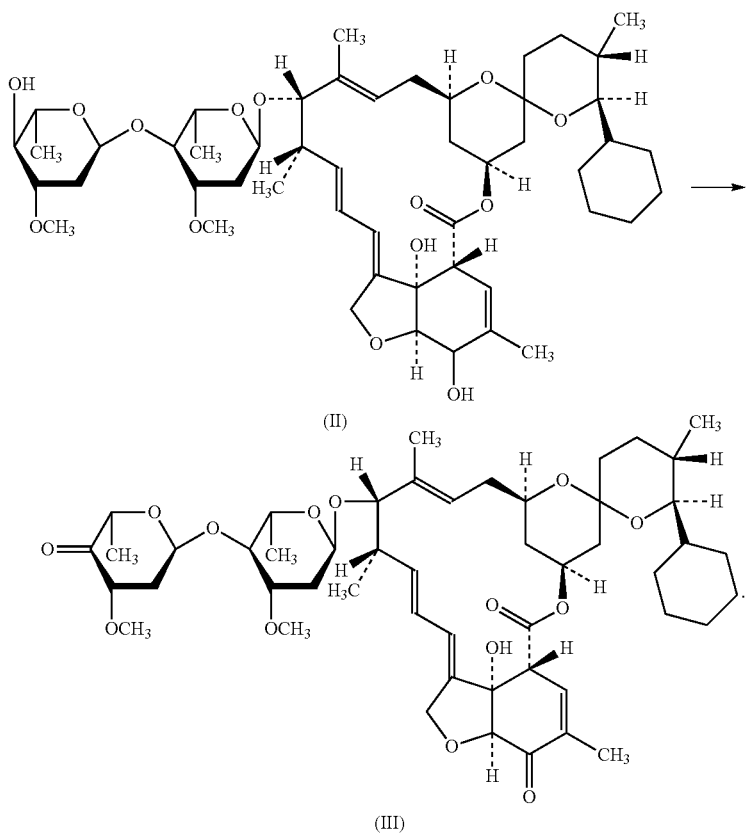

Preferably, dimethyl sulfoxide is used as the oxidant in the oxidation, which is carried out under the synergistic effect of dimethyl sulfoxide and an activator under basic condition. Wherein the activator is preferably selected from phenoxy phosphorodichloridate, oxalyl chloride, trifluoroacetic anhydride, acetic anhydride, and sulfur trioxide-pyridine complex, and the base is selected from triethylamine and N,N-diisopropylethylamine.

Also preferably, Dess-Martin reagent is used as the oxidant of the oxidation.

Preferably, the solvent in the oxidation is methylene dichloride, methenyl trichloride, toluene, acetone, and tetrahydrofuran.

Preferably, the reaction temperature is −78° C. to 30° C.

Referring to U.S. Pat. No. 6,906,184, the compound of formula (II) in the above mentioned oxidation is obtained by converting the double-bond at C-22, 23 position into single bond, via addition of the double bond, under the effect of Wilkinson catalyst:

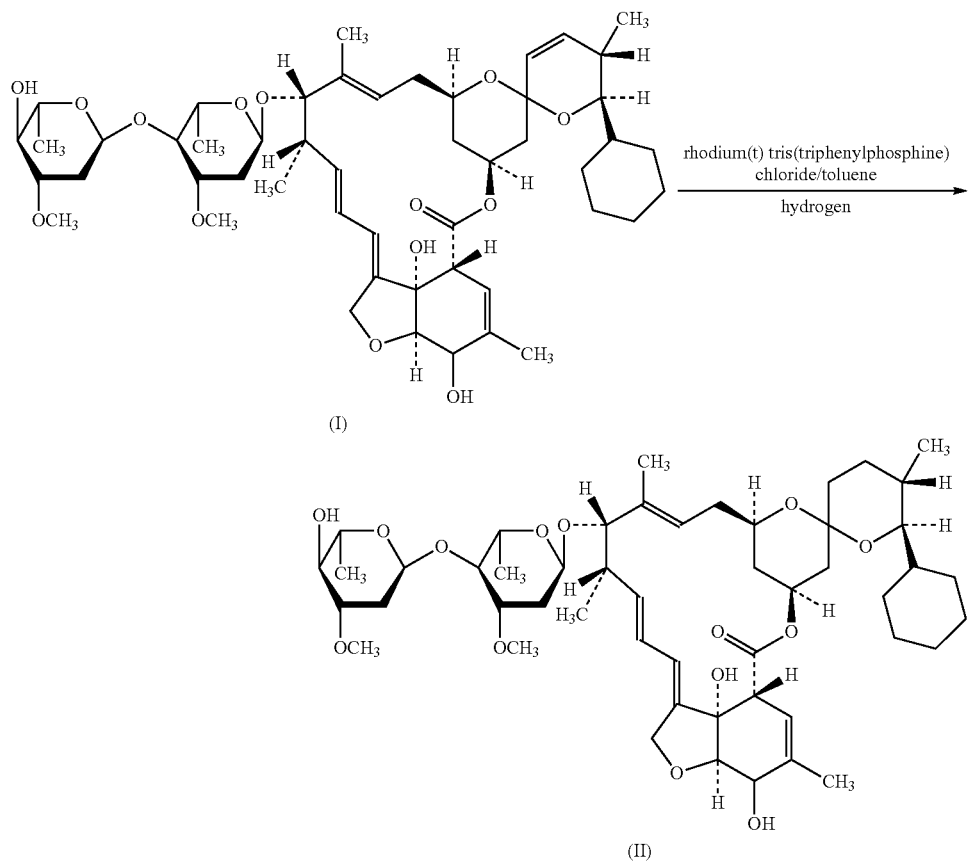

In another aspect of the present invention, there provides a method for the preparation of the compound of formula (IV), including the conversion of the compound of formula (III) and a nucleophile into the compound of formula (IV) under acidic condition:

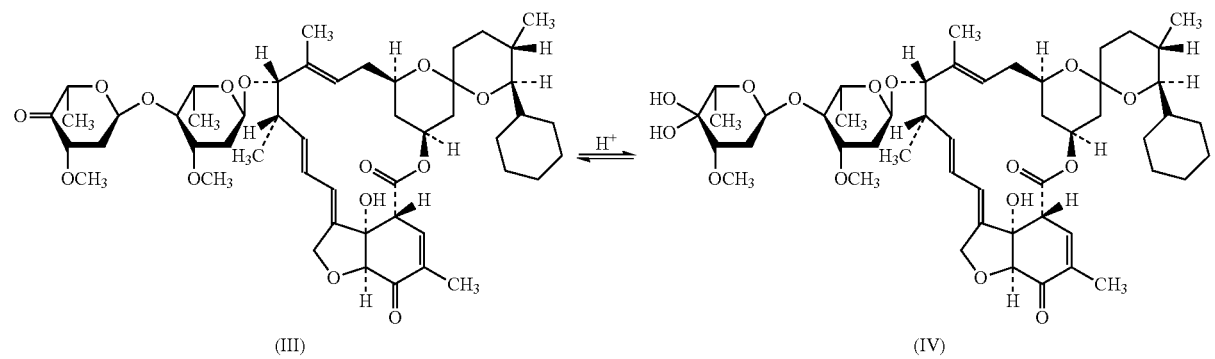

Preferably, the nucleophile used in the reaction is water.

The reaction is carried out under acidic condition, wherein such acidic condition is preferably formed by acidic silica gel, $C_1$-$C_8$ monobasic acids, $C_2$-$C_8$ dibasic acids, or $C_4$-$C_8$ tribasic acids.

In the reaction, the compound of formula (III) preferably undergoes nucleophilic addition with the nucleophile such as water under acidic condition, forming the addition product, a ketone-water compound, i.e. the compound of formula (IV). Such compound is thermodynamically unstable, and tends to be converted back into the former ketone by dehydration. Such addition is a reversible reaction, and the reaction equilibrium significantly tends to the reactant. During the separation process, the compound of formula (IV) tends to be converted back into the compound of formula (III) by dehydration, and thus is difficult to separate out. Also, the compound of formula (III) has equivalent effects with the compound of formula (IV), and thus there is no need to carry out purification.

In a further aspect of the present invention, there provides a method for the preparation of selamectin, including steps of forming selamectin from the compound of formula (III) or the compound of formula (IV) or mixtures thereof, via oximation and desugaring reaction:

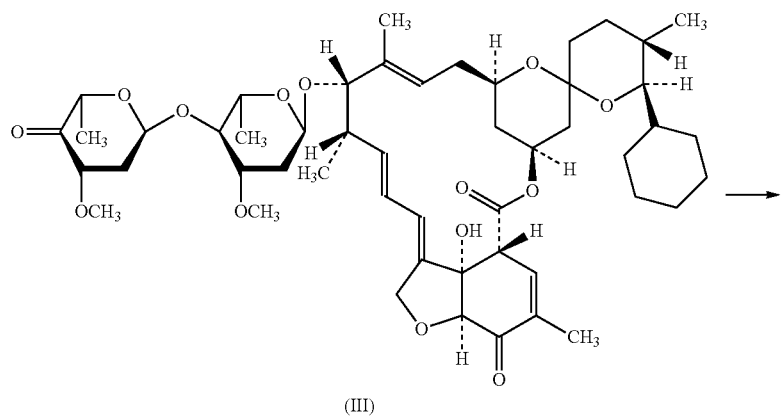

(III)

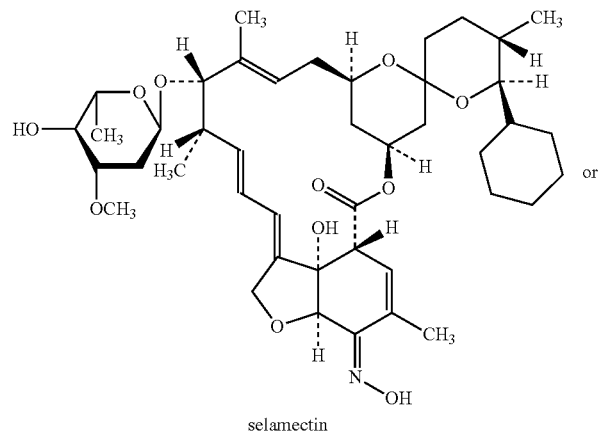

selamectin or

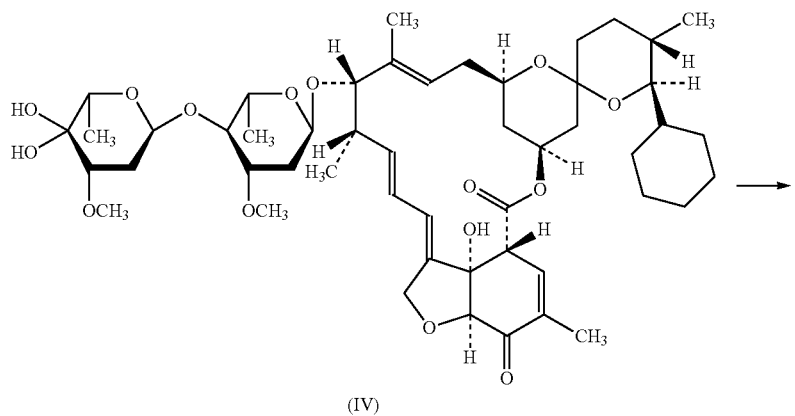

(IV)

-continued

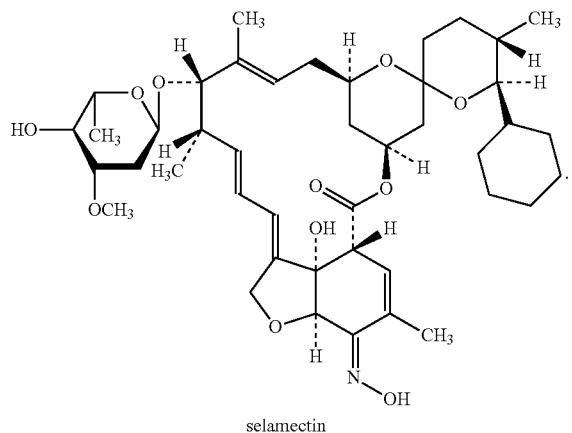

selamectin

Preferably, the reaction is carried out in a homogeneous system formed by a $C_1$-$C_3$ alcohol and dioxane and water or a homogeneous system formed by a $C_1$-$C_3$ alcohol and water.

Preferably, the temperature of the reaction is 0-60° C.

A preferred synthesis scheme of selamectin is as follows, wherein dimethyl sulfoxide is used as the oxidant in scheme 1, and Dess-Martin reagent is used as the oxidant in scheme 2.

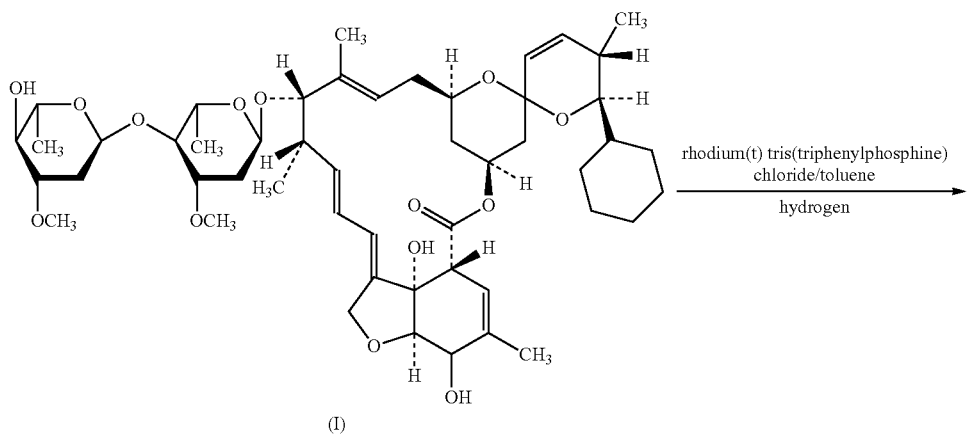

(I)

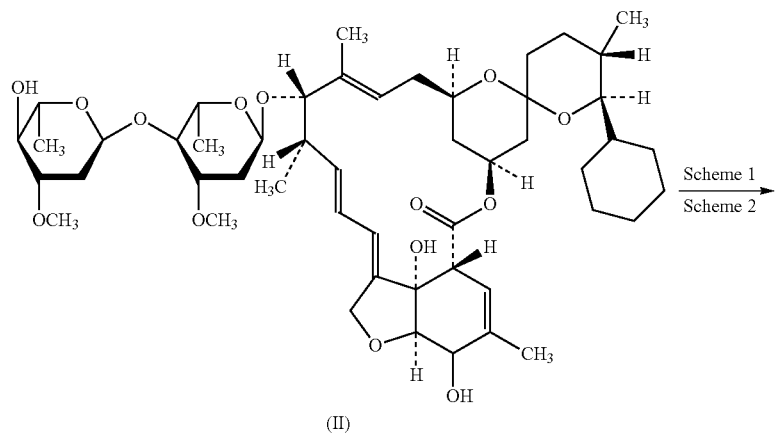

(II)

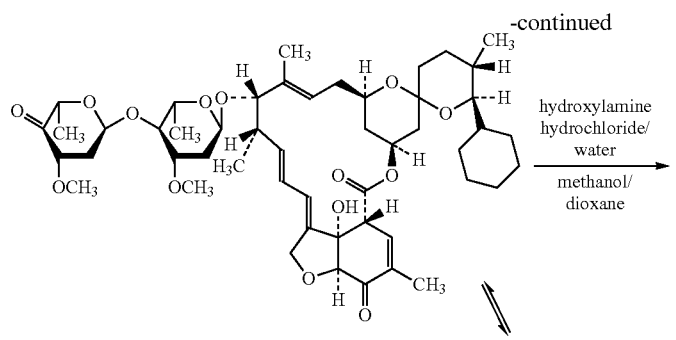

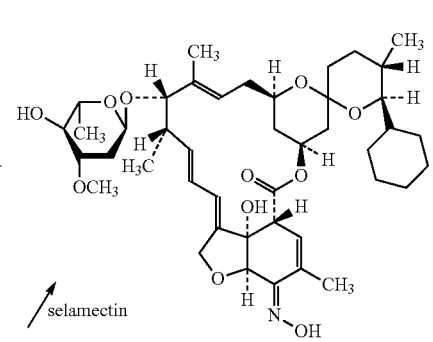

(III)

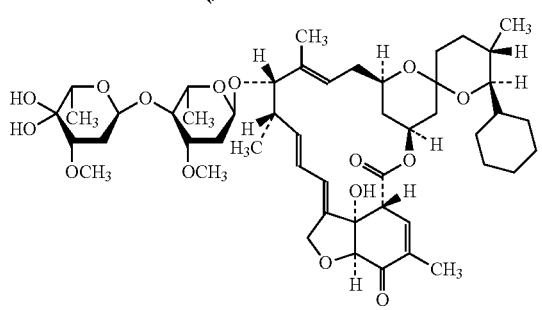

(IV)

In the first step of the above mentioned reaction, doramectin is preferably dissolved using toluene, as the solvent. The reaction is carried out at a pressure of 0-10 kg and a temperature of 20-60° C., under the effect of Wilkinson catalyst, rhodium tris(triphenylphosphine) chloride (I), and reaches its end point after 1-48 h. The compound of formula (II) is separated by filtration and removing of the solvent.

In the second step, methylene dichloride is preferably used as the solvent, although other organic solvents such as methenyl trichloride, toluene, acetone, tetrahydrofuran, etc., can also be used. Dimethyl sulfoxide is added with stirring, and is cooled to about 0° C. while stirring, and then triethylamine is added dropwise, the mixed solution is cooled to −35° C. to 25° C. after the addition of triethylamine is complete, and then phenoxy phosphorodichloridate is added dropwise, the temperature is maintained after the addition is complete. The reaction reaches its end point after about 0.5-4 h, and is quenched by adding aqueous solution of $NaHCO_3$. The obtained reactant is subject to layered extraction, the organic phase is collected and then concentrated and dried to obtain the compound of formula (III), in the form of yellowish substance. The compound of formula (III) can be converted into the compound of formula (IV), in the presence of a nucleophilic reagent under acidic condition. However, the inter-conversion between the compound of formula (III) and the compound of formula (IV) will not influence the third step and the quality of the final product.

In the third step, hydroxylamine hydrochloride is reacted with the compound of formula (III) or the compound of formula (IV) or mixtures thereof, in 0-60° C. water bath, for 1-48 h, to reach the end point, preferably under the effects of a mixed solvent of methanol/dioxane/water. Thereafter, methylene dichloride and water are added into the reaction liquid for extraction, the organic phase is collected and concentrated and dried, to obtain crude selamectin.

In comparison to prior arts, the present invention has the following advantages.

The present invention is a novel process developed on the basis of the processes described in prior art references, and overcomes the disadvantages of prior art processes and provides a novel method for the preparation of selamectin.

According to the present invention, selamectin is prepared via three-step chemical synthesis, using doramectin as the starting material. The first step, i.e. hydrogenation, involves the conversion of the double bond at the C-22, 23 position into single bond by addition reaction, under the effects of Wilkinson catalyst, with reference to U.S. Pat. No. 6,906,184. In the second step, i.e. oxidation, of the present invention, hydroxyl group at C-5 position is oxidized to ketone by using dimethyl sulfoxide, Dess-Martine reagent, etc., as the oxidant, while the hydroxyl group in C-4' sugar is oxidized to carbonyl, to obtain a novel intermediate for the preparation of selamectin. The oxidants are easy to after-treatment and have low pollution. The oximation and desugaring process in the third step, involves the oximation of the ketone at C-5 position, while C-4' desugars a sugar molecule, to obtain selamectin. In the present invention, the reaction period is significantly shortened by changing the types of the solvents. The processes according to the present invention is obviously superior to the hydrogenation, oxidation, oximation, and desugaring processes that described in the prior art references, rendering the overall yield of the present process is significantly improved, the present process period is shortened, the efficiency is significantly improved, and the pollution is reduced accordingly.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

EXAMPLES

The following examples are provided for the purpose of describing all aspects of the present invention completely, in order to illustrate the specific embodiments of the present invention, but are not limiting.

Example 1

Hydrogenation Reaction

3 L toluene was weighted into a clean and pressure-tested 5 L hydrogenation tank, the feed valve was opened and 300 g doramectin and 9 g rhodium tris(triphenylphosphine) chloride (I) were added into the tank with stirring. The feed inlet was closed and the air in the tank was purged with nitrogen for 3 times.

The hydrogen valve was opened, in order to keep the pressure in the tank to 3 kg. The temperature was raised until the inner temperature of the tank was 50° C., and this temperature was kept for 1-6 h. The hydrogen pressure in the tank was removed after the hydrogenation was completed. It was purged with nitrogen for 3 times, and then emptying. And then, the bottom valve was opened, and the materials in the tank were transferred into a flask. The solvent was removed by filtration, and a compound of formula (II) was separated (288 g, HPLC: 95.2%).

Example 2

Oxidation Reaction 100 g compound of the above formula (II) was weighted and dissolved into 1 L methylene dichloride. 188 g Dess-Martin reagent was added with vigorous stirring. The reaction was held at room temperature for 2 h, until reached the end point. The product was filtered with the assistance of diatomaceous earth, in order to remove insoluble solid residue. 500 mL aqueous solution of $NaHCO_3/Na_2S_2O_3$ (1:1) was added into the filtrate for washing. The aqueous phase was again washed with 200 mL methylene dichloride for one time. The organic phases were combined and washed with water for one time, and then dried with anhydrous magnesium sulfate for 30 min. The solid was filtered off, and the filtrate was concentrated to obtain light yellowish compound of formula (III) (96 g, HPLC: 89%).

The $^1H$ NMR and $^{13}C$ NMR data of the compound of formula (III) are determined as follows:

$^1H$ NMR (400 MHz, d-$CDCl_3$) δ: 0.81 (d, J=1.51 Hz, 3H), 0.87 (t, J=1.79, 3.69, 5.45 Hz, 1H), 1.19 (d, J=1.28, 1.63, 1.79, 2.57 Hz, 4), 1.21 (m, J=1.51, 1.63, 1.79 Hz, 2H), 1.28 (m, J=1.79, 3.89, 4.43 Hz, 7H), 1.39 (t, J=1.99, 5.45 Hz, 1H), 1.51 (m, J=0.81, 1.21, 1.63, 3.07 Hz, 10H), 1.63 (m, J=1.21, 1.28, 1.51, 2.31, 3.69, 4.81 Hz, 4H), 1.79 (m, J=0.87, 1.19, 1.21, 1.28, 5.45 Hz, 3H), 1.90 (t, 3H), 1.99 (m, J=1.39, 5.45 Hz, 1H), 2.14 (m, J=2.57, 4.19, 5.53 Hz, 1H), 2.31 (m, J=1.63, 3.69, 4.81, 5.02 Hz, 3H), 2.57 (m, J=1.19, 2.14, 3.96, 4.19, 5.53, 5.76 Hz, 2H), 3.07 (d, J=1.51 Hz, 1H), 3.34 (t, J=3.69, 3.89 Hz, 1H), 3.44 (s, 3H), 3.51 (s, 3H), 3.58 (m, J=6.59 Hz, 1H), 3.69 (m, J=0.87, 1.63, 2.31, 3.34 Hz, 2H), 3.86 (s, 1H), 3.89 (m, J=1.28, 3.34 Hz, 1H), 3.96 (s, J=2.57 Hz, 1H), 4.19 (m, J=2.14, 2.57 Hz, 1H), 4.43 (m, J=1.28 Hz, 1H), 4.74 (m, 2H), 4.81 (m, J=1.63 Hz, 1H), 5.02 (d, J=2.31 Hz, 1H), 5.45 (m, J=0.87, 1.39, 1.79, 1.99 Hz, 1H), 5.53 (d, J=2.14, 2.57 Hz, 1H), 5.76 (m, J=2.57, 5.95 Hz, 2H), 5.95 (m, J=5.76 Hz, 1H), 6.59 (t, J=3.58 Hz, 1H); $^{13}C$ NMR (400 MHz, d-$CDCl_3$) δ: 13.91, 15.17, 15.43, 17.42, 18.36, 20.09, 24.73, 26.58, 27.00, 28.06, 30.66, 31.29, 34.14, 34.61, 35.67, 36.96, 38.57, 39.43, 39.85, 41.11, 46.62, 56.44, 58.32, 67.02, 67.10, 69.30, 69.85, 70.78, 78.05, 78.62, 79.19, 80.82, 81.16, 81.83, 81.92, 94.87, 97.51, 98.03, 118.41, 121.87, 124.70, 134.98, 136.82, 137.98, 138.99, 172.28, 192.09, 205.92.

Example 3

Oxidation Reaction 100 g compound of the above formula (II) was weighted and dissolved into 1 L methylene dichloride. 48.5 mL dimethyl sulfoxide was added with vigorous stirring. The solution was cooled to a temperature of −60° C. with stirring, and then 62.6 mL trifluoroacetic anhydride, which had been diluted by methylene dichloride, was added dropwise. After addition, it was stirred for 30 min, and then 123 mL triethylamine was added into the reaction liquor dropwise. The reaction was held at −60° C. for 2 h, until reached the end point. The reaction liquid was washed twice with 200 mL water. The organic phase was dried with anhydrous magnesium sulfate for 30 min. The solid was filtered off, and the filtrate was concentrated to obtain light yellowish compound of formula (III) (93 g, HPLC: 85%).

Example 4

Oxidation Reaction 100 g compound of the above formula (II) was weighted and dissolved into 1 L toluene. 46 mL dimethyl sulfoxide was added with vigorous stirring. The solution was cooled to a temperature of −65° C. with stirring, and then 45.3 mL oxalyl chloride, which had been diluted by toluene, was added dropwise. After addition, it was stirred for 30 min at −65° C., and then the inner temperature was controlled and 120 mL triethylamine was added into the reaction liquor dropwise under such temperature. The reaction was held for 1 h, until reached the end point. The reaction liquid was washed with 5% sodium hydrogen carbonate for one time. The product was layered and the organic phase was washed with water again for one time and dried with anhydrous sodium sulfate for 1 h. The solid was filtered off, and the filtrate was concentrated to obtain light yellowish compound of formula (III) (95.2 g, HPLC: 55.3%).

Example 5

Oxidation Reaction 100 g compound of the above formula (II) was added into a clean 2 L four-neck flask and dissolved with 1.0 L methylene dichloride. 45 mL dimethyl sulfoxide was added into the four-neck flask with continuous stirring. The solution was cooled to a temperature of about 0° C. with stirring, and then 86 mL triethylamine was added dropwise. After addition, the mixed solution was cooled to −35° C., and then 47 mL phenoxy phosphorodichloridate solution, which has been diluted with 200 mL methylene dichloride, was added. After addition, the reaction was held at −30° C. for 2 h, until reached the end point. And then 400 mL 5% aqueous solution of sodium hydrogen carbonate was weighted into the flask. It was stirred at room temperature for 30 min. The product was layered and the upper organic phase was collected. The aqueous phase was back-extracted with 300 mL methylene dichloride for one time. The organic phases were combined and then washed with 400 mL water for one time, and dried with 100 g anhydrous sodium sulfate. The anhydrous sodium sulfate was filtered off, and the solvent was concentrated to dry at 45° C., to obtain light yellowish compound of formula (III) (95 g, HPLC: 93%).

Example 6

Oxidation Reaction 10 g compound of the formula (II) and 5.8 mL N,N-diisopropyl ethylamine were added into the mixed solvent of 20 mL anhydrous dimethyl sulfoxide and 80 mL anhydrous methylene dichloride. It was cooled to 0° C., and 5.3 g sulfur trioxide-pyridine complex was added with vigorous stirring. The reaction solution was raised to room temperature, and the stirring was continued until reached the end point. 50 mL saturated aqueous solution of sodium hydrogen carbonate and 20 mL methylene dichloride were added into the reaction liquid. It was held until layered, and the aqueous phase was back-extracted with 80 mL methylene dichloride. The methylene dichloride phases were combined, and were washed with 50 mL saturated aqueous solution of sodium hydrogen carbonate for one time and 50 mL saturated saline for one time, respectively, and then was dried over anhydrous magnesium sulfate for 30 min. It was filtered at reduced pressure, and concentrated, to obtain light yellowish compound of formula (III) (9.1 g, HPLC: 85%).

Example 7

Oximation and Desugaring Reaction 252 g the compound of formula (III) was dissolved into 1.8 L methanol and 1.8 L dioxane. Aqueous solution of 300 g hydroxylamine hydrochloride in 500 mL purified water was added with stirring. The inner temperature of the reaction liquid was raised to 40° C. for 4 h, until reached the end point. 1 L water and 2 L methylene dichloride were added into the reaction liquid, in order to quench the reaction. It was layered and extracted. The aqueous phase was back-extracted with 400 mL methylene dichloride. The organic phases were combined and washed with 400 mL water for one time. The organic phases were collected and dried over 100 g anhydrous sodium sulfate, and then filtered under reduced pressure. The filtrate was concentrated to dry, to obtain crude selamectin (201 g, HPLC: 81.2%).

Example 8

Oximation and Desugaring Reaction 100 g the compound of formula (III) was dissolved into 800 mL isopropanol. 100 g hydroxylamine hydrochloride in 200 mL water was added with stirring. The inner temperature of the reaction liquid was raised to 60° C. for 2.5 h, until reached the end point. 1 L water and 400 mL methylene dichloride were added into the reaction liquid to quench the reaction. It was layered and extracted. The aqueous phase was back-extracted with 500 mL methylene dichloride. The organic phases were combined and washed with 500 mL water for one time. The organic phases were collected and dried over 100 g anhydrous sodium sulfate, and then filtered. The filtrate was concentrated to dry, to obtain crude selamectin (80 g, HPLC: 65.2%).

Example 9

Oximation and Desugaring Reaction 50 g the compound of formula (III) was dissolved into 400 mL methanol and 400 mL dioxane, and the inner temperature was cooled to 10° C. 50 g hydroxylamine hydrochloride in 50 mL purified water was added with stirring. The inner temperature of the reaction liquid was controlled to 10° C.±2° C. for 168 h, until reached the end point. 400 mL water and 1000 mL methylene dichloride were added into the reaction liquid to quench the reaction. It was layered and extracted. The aqueous phase was back-extracted with 200 mL methylene dichloride for one time. The organic phases were combined and washed with 200 mL water for one time. The organic phases were collected and dried over 50 g anhydrous sodium sulfate, and then filtered under reduced pressure. The filtrate was concentrated to dry, to obtain crude selamectin (46.8 g, HPLC: 80.9%).

Example 10

Preparation of the Compound of Formula (IV) from the Compound of Formula (III)

0.5 g the compound of formula (III) was weighted in a single-neck flask, and 4 mL acetonitrile and 1 mL water were added into the flask. Also, 0.25 g acidic silica gel was added into the flask at room temperature. It was stirred at room temperature for 3 h, and filtered to remove residues. The filtrate was collected and concentrated to obtain about 0.46 g product, in the form of white solid. It is determined by HPLC that the content of the compound of formula (IV) is 16%, and that of the compound of formula (III) is 83.2%. The MS data of the compound of formula (IV) is as follows: MS (m/z): 936 [M+Na].

Example 11

Preparation of the Compound of Formula (IV) from the Compound of Formula (III)

0.15 g the compound of formula (III) was weighted in a single-neck flask, and 2 mL acetonitrile and 1 mL water were added into the flask. Then a drop of 10% acetic acid was added into the flask at room temperature. It was stirred at room temperature for 2 h, and filtered to remove residues. The filtrate was collected and concentrated to obtain about 0.13 g product, in the form of white solid. It is determined by HPLC that the content of the compound of formula (IV) is 12.3%, and that of the compound of formula (III) is 87.1%.

Example 12

Oximation and Desugaring Reaction 0.2 g of the mixture of the compound of formula (III) and the compound of formula (IV), obtained from Example 10, was dissolved into 2 mL methanol and 2 mL dioxane. 0.2 mL purified water and 0.2 g hydroxylamine hydrochloride were added with stirring. The inner temperature of the reaction liquid was raised to 40° C. for 4 h, until reached the end point. 5 mL water and 5 mL methylene dichloride were added into the reaction liquid to quench the reaction. It was layered and extracted. The aqueous phase was back-extracted with 5 mL methyleme dichloride for one time. The organic phases were combined and washed with 5 mL water for one time. The organic phases were collected and dried over 1 g anhydrous sodium sulfate, and then filtered under reduced pressure. The filtrate was concentrated to dry, to obtain crude selamectin (0.19 g, HPLC: 78.6%).

Example 13

Preparation of the Compound of Formula (III) from the Compound of Formula (IV)

The aqueous acetonitrile solution of the compound of formula (IV) (HPLC content of 98.5%), prepared by reversed phase C18 silica gel, was converted into the compound of formula (III) by being concentrated at 40° C. under reduced pressure.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A compound represented by the following formula (III)

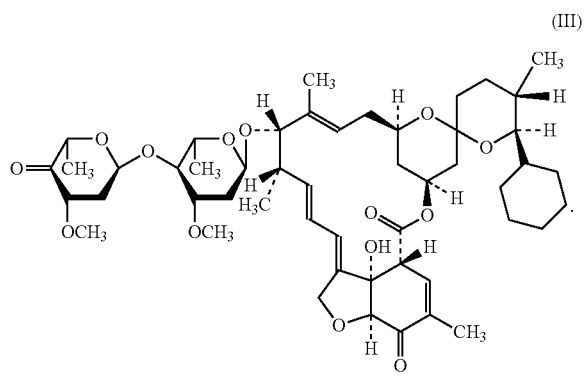

2. A method for preparation of the compound of formula (III) according to claim 1, characterized in that the compound of formula (III) is prepared from the compound of formula (II) by an oxidation reaction:

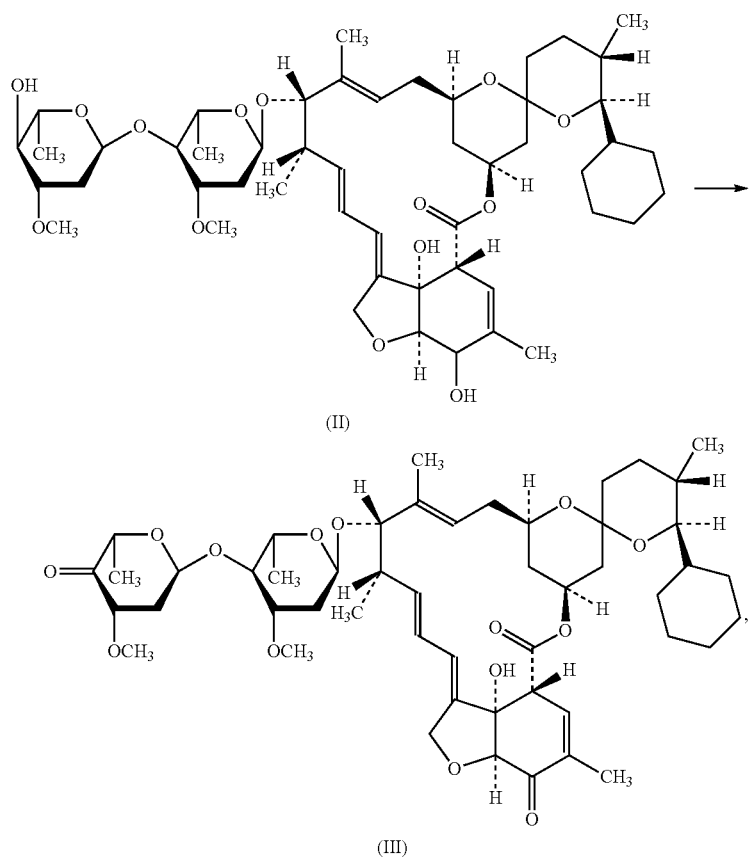

wherein an oxidant used in the oxidation reaction is dimethyl sulfoxide, and an activator used the oxidation reaction is phenoxy phosphorodichloridate.

3. The method according to claim 2, characterized in that the oxidation reaction is carried out under basic condition.

4. The method according to claim 2, characterized in that a solvent used in the oxidation reaction is selected from dichloromethane, trichloromethane, toluene, acetone, and tetrahydrofuran, and a temperature for the oxidation reaction is $-78°$ C. to $30°$ C.

5. A compound represented by the following formula (IV):

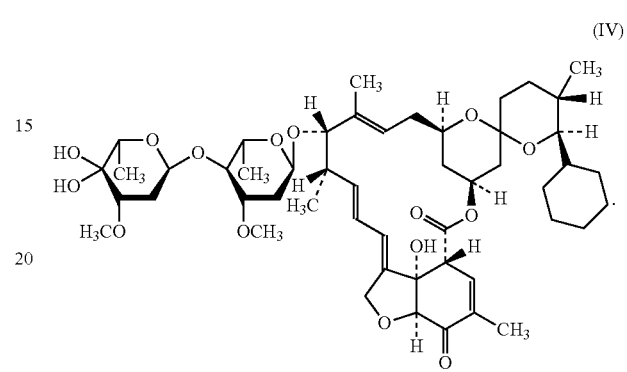

6. A method for preparation of the compound of formula (IV) according to claim 5, characterized in that a compound of formula (III) is converted into the compound of formula (IV) with a nucleophilic reagent under acidic condition:

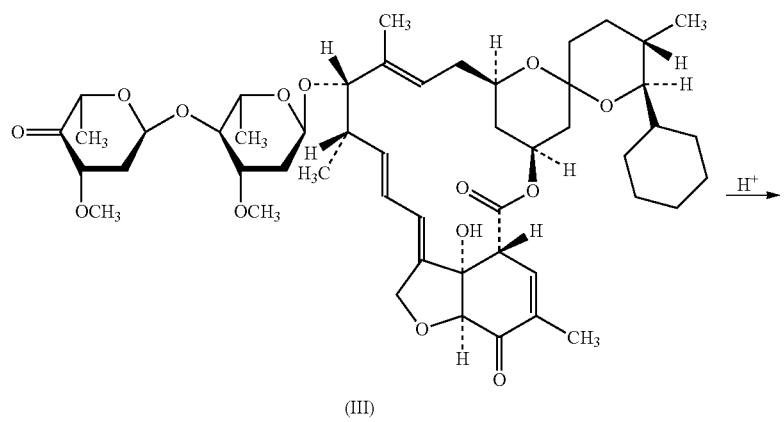

(III)

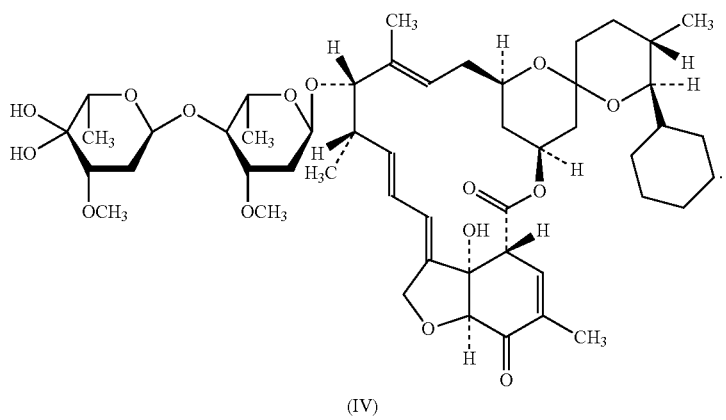

(IV)

7. The method according to claim 6, characterized in that the nucleophilic reagent is selected from water, and the acidic condition is formed by acidic silica gel, $C_1$-$C_8$ monobasic acids, $C_2$-$C_8$ dibasic acids, or $C_4$-$C_8$ tribasic acids.

8. A method for preparation of selamectin, characterized in that the method comprises steps wherein a compound of formula (III) is prepared from the compound of formula (II) by an oxidation reaction:

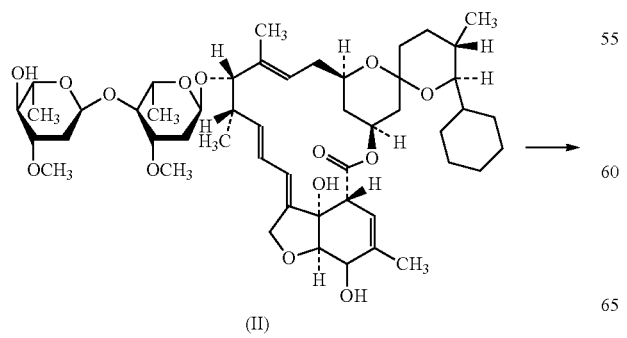

(II)

-continued

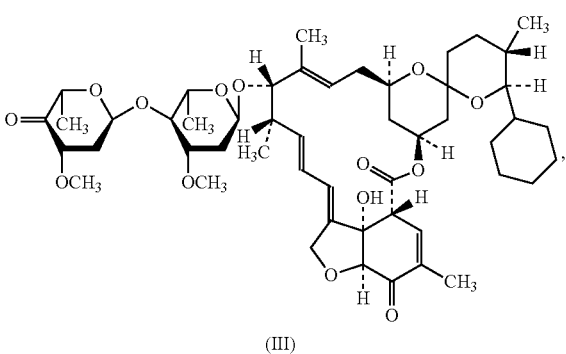

(III)

wherein an oxidant used in the oxidation reaction is dimethyl sulfoxide, and an activator used the oxidation reaction is phenoxy phosphorodichloridate, and the compound of Formula (III) or a compound of formula (IV) or mixture thereof is converted to selamectin by an oximation and a desugaring reaction:

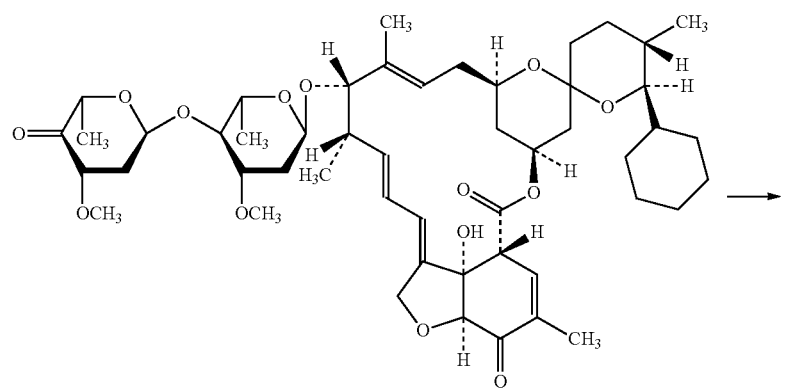
(III)
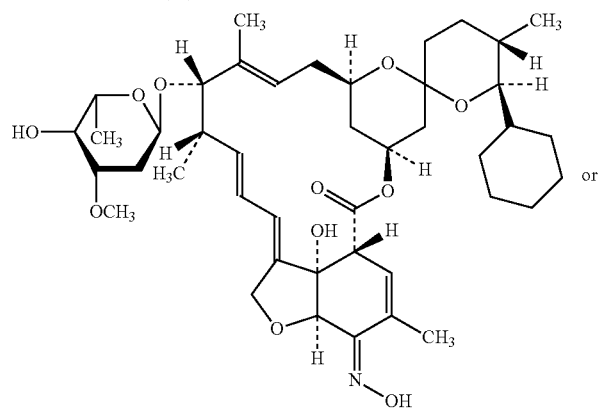
selamectin
or
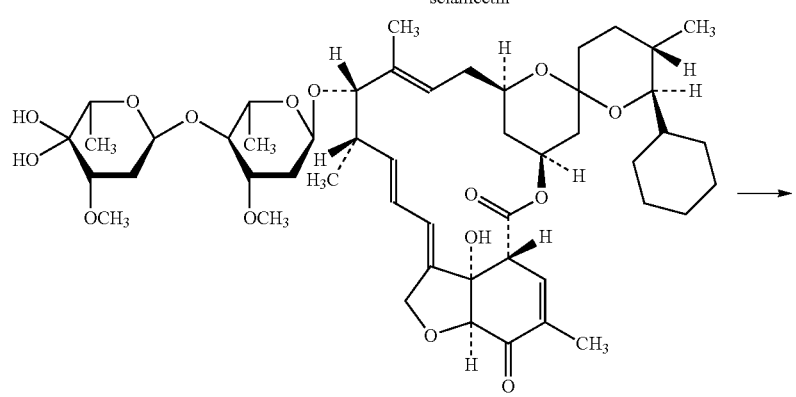
(IV)
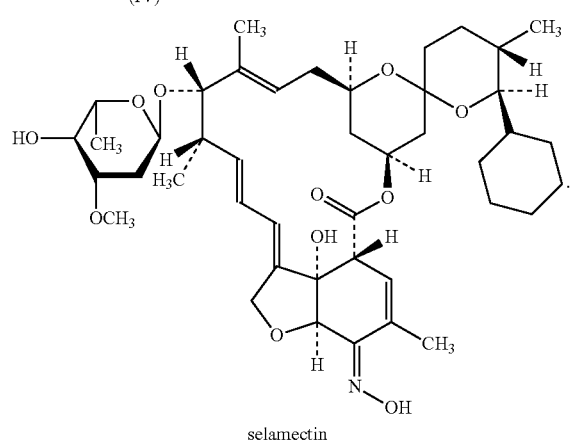
selamectin

9. The method according to claim 8, characterized in that a solvent used in the oximation and desugaring reaction is selected from a homogeneous system formed by a $C_1$-$C_3$ alcohol and dioxane and water or a homogeneous system formed by a $C_1$-$C_3$ alcohol and water, and a reaction temperature is 0-60° C.

\* \* \* \* \*